United States Patent [19]

Kinkade

[11] Patent Number: 4,590,314
[45] Date of Patent: May 20, 1986

[54] CATALYTIC PROCESS FOR THE PRODUCTION OF ALCOHOLS FROM CARBON MONOXIDE, HYDROGEN AND OLEFINS

[75] Inventor: Nancy E. Kinkade, St. Albans, W. Va.

[73] Assignee: Union Carbide Corporation, Danbury, Conn.

[21] Appl. No.: 671,886

[22] Filed: Nov. 19, 1984

Related U.S. Application Data

[63] Continuation-in-part of Ser. No. 567,244, Dec. 30, 1983, abandoned.

[51] Int. Cl.$^4$ .................. C07C 29/16; C07C 31/12
[52] U.S. Cl. ............................ 568/909; 502/220; 568/451
[58] Field of Search ............................ 568/909

[56] References Cited

U.S. PATENT DOCUMENTS

| | | | |
|---|---|---|---|
| 2,490,488 | 12/1949 | Stewart | 518/714 |
| 2,671,119 | 3/1954 | Mertzweiller | 260/638 |
| 2,709,714 | 5/1955 | Mertzweiller | 260/638 |
| 2,976,254 | 3/1961 | Mason et al. | 252/439 |
| 3,118,954 | 1/1964 | Robbins et al. | 260/638 |
| 3,239,569 | 3/1966 | Slaugh et al. | 260/632 |
| 3,326,956 | 6/1967 | Davies et al. | 260/449.5 |
| 3,594,425 | 7/1971 | Brader et al. | 568/909 |
| 3,631,111 | 12/1971 | Tucci | 568/909 |
| 4,122,110 | 10/1978 | Sugier et al. | 260/449.5 |
| 4,151,190 | 4/1979 | Murchison et al. | 260/449 R |
| 4,199,520 | 4/1980 | Cosby et al. | 260/429 R |
| 4,199,522 | 4/1980 | Murchison et al. | 518/714 |
| 4,235,798 | 11/1980 | Bartley et al. | 260/449 R |
| 4,235,801 | 11/1980 | Bhasin | 260/449.6 R |
| 4,291,126 | 9/1981 | Sugier et al. | 518/713 |
| 4,361,711 | 11/1982 | Blaskie et al. | 568/909 |
| 4,377,643 | 3/1983 | Pesa et al. | 518/713 |
| 4,380,589 | 4/1983 | Murchison et al. | 518/714 |

FOREIGN PATENT DOCUMENTS

| | | |
|---|---|---|
| 1159474 | 12/1983 | Canada . |
| 0119609 | 9/1984 | European Pat. Off. . |
| 1228947 | 4/1971 | United Kingdom . |
| 2065490 | 7/1981 | United Kingdom . |
| 2065491 | 7/1981 | United Kingdom . |

OTHER PUBLICATIONS

"Chemical Week"—Oct. 31, 1984, p. 96.
"Chemical Week"—Nov. 7, 1984, pp. 28-29.
J. F. Shultz et al. "Bureau of Mines," Report of Investigations, No. 6974, U.S. Dept. of Interior (1967).
J. Falbe Book, "New Synthesis with Carbon Monoxide" (1980) pp. 57-68, 167 and 168.
G. A. Mills et al., "Catalysis Reviews," vol. 8, pp. 159-210 (1973).

*Primary Examiner*—J. E. Evans
*Attorney, Agent, or Firm*—R. J. Finnegan

[57] ABSTRACT

A process is disclosed for the production, selectively, of $C_{n+1}$ alcohols from a $C_n$ olefin. The process comprises reacting the $C_n$ olefin with carbon monoxide and hydrogen in the presence of a catalyst consisting essentially of molybdenum sulfide and an alkali metal or alkaline earth metal compound.

18 Claims, No Drawings

CATALYTIC PROCESS FOR THE PRODUCTION OF ALCOHOLS FROM CARBON MONOXIDE, HYDROGEN AND OLEFINS

BACKGROUND OF THE INVENTION

This application is a continuation-in-part of prior U.S. patent application Ser. No. 567,244, filed Dec. 30, 1983, now abandoned.

FIELD OF THE INVENTION

This invention generally relates to a catalytic process for the production of alcohols directly from carbon monoxide, olefins and hydrogen; and more particularly to the use of an alkali metal or alkaline earth metal containing molybdenum sulfide heterogeneous catalyst for selectively converting carbon monoxide, hydrogen and an olefin to an alcohol containing one more carbon atom than the starting olefin.

DESCRIPTION OF THE PRIOR ART

It is known that carbon monoxide, hydrogen and olefins may be reacted in the presence of homogeneous catalysts to produce hydrocarbons and various oxygenated compounds such as aldehydes and alcohols.

For example, U.S. Pat. No. 3,239,569 discloses a homogeneous catalyst comprising phosphine-modified cobalt carbonyl. The catalyst is said to be useful for the hydroformylation of olefins to aldehydes and/or alcohols at pressures less than 1000 psig.

Heterogeneous catalysts are known to be useful in synthesis gas reactions for producing various oxygenated products. For example, U.S. Pat. No. 4,361,711 discloses a solid rhodium oxide-based heterogeneous catalyst for the production of $C_{n+1}$ alcohols from a $C_n$ olefin and synthesis gas (i.e., predominantly a mixture of carbon monoxide and hydrogen). The disclosed catalyst has the formula:

$$A_aRhO_x$$

wherein "A" is Fe, Zn, Ir, Ru, Nb, Cr, Mn, and/or Pt. "a" is 0.001 to 10 and "x" is greater than zero but less than a number sufficient to satisfy the valence requirements of the other elements present in the composition when in a fully oxidized state. The patent discloses that the catalyst operates at temperatures at or above 100° C. and pressures at or above 150 psig. Other heterogeneous catalysts for producing alcohols are also known. For example, U.S. Pat. No. 3,326,956 describes a process for producing oxygenated hydrocarbons, especially methyl alcohol, which comprises contacting, at elevated temperatures and pressures, a mixture of hydrogen, carbon monoxide and carbon dioxide with a solid catalyst comprising the product of partly reducing the mixed oxides of copper, zinc and chromium.

More recently, U.S. Pat. No. 4,377,643 discloses a catalytic process for converting synthesis gas to alcohols and alkanes comprising contacting carbon monoxide and hydrogen with a catalyst of the formula:

$$A_aRu_bCu_cM_dN_zO_x$$

wherein A is an alkali metal, M is Rh, Ir, Pd, Pt or mixtures thereof, a is about 0.002 to about 0.5, b is about 0.5 to about 3, c is about 0.5 to about 3, d is about 0.05 to about 0.5, z is a level of 0 to about 1 weight % and x is the number of oxygens needed to fulfill the valence requirements of the other elements.

U.S. Pat. No. 4,122,110 discloses a process for manufacturing alcohols, particularly linear, saturated primary alcohols, by the reaction of carbon monoxide (optionally with carbon dioxide being present also) and hydrogen in the presence of a catalyst containing four essential elements: copper, cobalt, a third metal selected from chromium, iron, vanadium and manganese, and a fourth metal which is an alkali metal; and optionally zinc. U.S. Pat. No. 4,291,126 discloses a related catalyst containing 20–60% copper, 5–50% cobalt, 5–30% of a metal selected from chromium, iron, vanadium and manganese, 5–40% of a rare earth element, 0.1–5% of an alkali or alkaline earth metal and, optionally, zinc and/or a noble Group VIII metal and/or a binder.

U.S. Pat. No. 4,199,520 discloses a rhodium catalyst which is useful for the manufacture of polyhydric alcohols, particularly ethylene glycol, from synthesis gas and which comprises a rhodium carbonyl sulfur cluster compound, the anion of which may be represented by the following empirical formula $[Rh_{17}(S)_2(CO)_{32}]^{-3}$ and the cation of which includes alkali metals.

U.S. Pat. No. 4,235,798 discloses a process for selectively preparing a mixture of two-carbon atom oxygenated hydrocarbons (i.e., acetic acid, ethyl alcohol and acetaldehyde) by contacting hydrogen and carbon monoxide with a solid catalyst comprising rhodium in combination with one or more alkali metals under reaction conditions to favor the formation of such products.

U.S. Pat. No. 4,235,801 discloses a process for producing ethyl alcohol from synthesis gas employing a catalyst essentially comprising rhodium and iron.

Molybdenum-based catalysts have also been used to catalyze a variety of reactions such as desulfurization, denitrofication and hydrogenation reactions. For example, U.S. Pat. No. 2,490,488 discloses the use of a molybdenum sulfide catalyst promoted with "minor proportions" of an alkali metal oxide, hydroxide or carbonate to produce liquid hydrocarbons and organic oxygen-containing compounds from carbon monoxide and hydrogen. The preferred amount of the alkali promoter, according to the patent, is about 0.5 to 5 weight percent based on the weight of molybdenum sulfide, or 2–20 mole percent when the promoter is potassium hydroxide. Carbon monoxide and hydrogen are said to be converted to normally liquid hydrocarbons and unspecified organic oxygen-containing compounds utilizing such catalyst.

U.S. Pat. No. 4,199,522 discloses a process for the production of $C_2$–$C_4$ olefinic hydrocarbons from synthesis gas using a catalyst consisting essentially of 1–95% by weight of at least one material selected from the group consisting of the sulfide, oxide and metal of molybdenum, tungsten, rhenium, ruthenium, nickel, palladium, rhodium, osmium, iridium and platinum and 0.05–50% by weight of at least one material selected from the group consisting of the hydroxide, oxide or salt of Li, Na, K, Rb, Cs, Mg, Ca, Sr, Ba and Th. U.S. Pat. No. 4,151,190 discloses a similar catalyst. There is no disclosure in either patent that such a catalyst produces oxygenated products and both processes are typically conducted at a GHSV of about 300 hr$^{-1}$.

A number of prior art references discloses so-called oxo processes which include the hydrogenation of aldehydes to alcohols in the presence of supported and unsupported molybdenum sulfide catalysts at elevated temperatures and pressures. The starting aldehydes are produced in the first step of the oxo process by carbonylating an olefin by reaction with carbon monoxide and hydrogen. These references include French Pat. No. 1,315,275 and U.S. Pat. Nos. 2,709,714, 2,813,911, 2,976,254, and 3,118,954.

J. P. Shultz, et al., Bureau of Mines Report of Investigations, No. 6974, U.S. Dep't. of the Interior (1967) report that molybdenum oxide and sulfide, used as methanation catalysts, produce up to 20% of the products as two to four-carbon atom hydrocarbons. However, there is no disclosure in this article concerning alcohols or any other oxygenated products from such systems.

In addition to the foregoing, published prior art, the present inventor is aware of an unpublished study, by a colleague, of catalysis by molybdenum sulfide. During that study, he observed that alcohols may be produced from carbon monoxide and hydrogen using a molybdenum sulfide catalyst containing small amounts (up to about 0.30 mole per mole of molybdenum) of an alkali such as potassium hydroxide. One experimental run (at 250° C., 400 psig. a $CO/H_2$ molar ratio of $\frac{1}{8}$, a GHSV of 3000 $hr^{-1}$ and a potassium loading of about 0.15–0.18 mole per mole of molybdenum) produced the following results:

SELECTIVITIES (%)

methyl alcohol: 46
ethyl alcohol: 26
n-propanol: 1
methane: 27

Rate of total alcohol production=1.8 pounds per cubic foot of catalyst per hour. In another experimental run, under the same conditions and employing a molybdenum sulfide/KOH catalyst prepared to contain about 0.3 mole potassium per mole of molybdenum, the following results were obtained:

SELECTIVITIES (%)

methyl alcohol: 35
ethyl alcohol: 19
n-propanol: 9
methane: 37

Rate of total alcohol production=1.9 pounds per cubic foot of catalyst per hour.

It has now been found that, under appropriate conditions and with certain catalysts, one can produce selectively mixtures of linear, primary $C_1$–$C_5$ alcohols from synthesis gas. This is the subject of a commonly-assigned U.S. patent application Ser. No. 567,243, filed Dec. 30, 1983 in the name of the same inventor entitled "Process for Producing Alcohols from Carbon Monoxide and Hydrogen Using an Alkali-Molybdenum Sulfide Catalyst". The present invention is based on the discovery that when an olefin is fed to the reaction, in addition to synthesis gas, the olefin starting material is selectively converted to an alcohol containing one more carbon atom than the starting olefin and that the formation of the linear, primary $C_1$–$C_5$ alcohols, such as that which might be considered to be attributed to the conversion of synthesis gas directly to alcohols by way of the process described in said application Ser. No. 567,243, is reduced.

SUMMARY OF INVENTION

The present invention is a process for the preparation of alcohols by reacting one or more olefins with carbon monoxide and hydrogen in the presence of a heterogeneous catalyst which consists essentially of molybdenum sulfide and an alkali compound selected from the group consisting of alkali metal and alkaline earth metal compounds and mixtures thereof to selectively convert the olefin starting material to an alcohol having one more carbon atom then the starting olefin.

DESCRIPTION OF THE PREFERRED EMBODIMENTS

The process of the present invention selectively converts an olefin starting material to an alcohol having one more carbon atom than the starting olefin, by reaction with carbon monoxide and hydrogen in the presence of an alkali-containing molybdenum sulfide catalyst. More than one olefin starting material may be reacted to produce more than one corresponding alcohol. Generally, for each starting olefin having n carbon atoms (n representing a positive integer of at least 2), the desired product resulting from reaction with carbon monoxide and hydrogen is a corresponding $C_{n+1}$ alcohol. Normally produced as non-alcohol by-products are $C_n$ and higher saturated hydrocarbons, ketones, esters and aldehydes. The conversion of synthesis gas directly to alcohols by way of the process which is described in the above-mentioned, commonly-assigned patent application Ser. No. 567,243 is generally incompletely suppressed and under such circumstances, $C_1$–$C_5$ alcohols and hydrocarbons from such a reaction are also produced, albeit to a lesser degree. Thus it is to be understood that the process of this invention produces an alcoholic product having a different composition than is produced by the process carried out in the absence of any olefin starting material. For example, the alcohol product of this invention will contain more $C_{n+1}$ alcohol, as a result of the selective conversion of the $C_n$ olefin starting material to said $C_{n+1}$ alcohol, in contrast to that amount of the same type of $C_{n+1}$ alcohol that might be produced directly from synthesis gas by a comparative process carried out in the absence of the olefin starting material. Indeed the selective conversion of the olefin starting material to its corresponding $C_{n+1}$ alcohol can be readily confirmed by comparing the amount of $C_{n+1}$ alcohol produced by the process of this invention in any given instance with the amount of such $C_{n+1}$ alcohol that might be produced by the process when carried out in the absence of any olefin starting material.

In its broadest aspects therefore, the process of the present invention comprises reacting a gas feed of one or more $C_n$ olefins with a mixture of carbon monoxide and hydrogen in the presence of a catalyst consisting essentially of molybdenum sulfide and a compound selected from the group consisting of alkali metal and alkaline earth metal compounds and mixtures thereof, under certain reaction conditions, to selectively produce $C_{n+1}$ alcohol from the $C_n$ olefin starting material.

For instance, the process of the present invention is useful for the production of propanol from ethylene and is especially useful for the production of iso-butanol and n-butanol from propylene. However, it is expected that the present invention is also useful for the production of any aliphatic $C_{n+1}$ alcohol having at least 3 carbon atoms (i.e., "n"=2) from the corresponding $C_n$ olefin starting material. Preferably, the olefin is a terminal olefin which may be unsubstituted or substituted, branched or straight-chain; examples of preferred terminal olefins are ethylene, propylene, 1-butene, 1-pentene, 1-hexene, 2-ethyl-1-hexene, 1-heptene, 1-octene, 1-nonene, 1-decene, 1-undecene, 1-dodecene, and the like.

In general when the $C_n$ olefin starting material is propylene or a higher olefin, the $C_{n+1}$ alcohol product will comprise a mixture of normal- and iso-alcohols. For instance, it has been observed that in producing butanol from propylene, the normal to iso-butanol ratio can be as low as about 2 to 1, while ratios of at least 5 to 1 and higher can be readily attained. In the production of propanol from ethylene only the normal isomer has been observed.

The process of this invention is extremely beneficial in that it provides one with a wide degree of processing latitude for obtaining a huge variety of alcohol products, as well as a simple method for controlling the composition of the alcohol product that might be desired. For example, control over the reaction conditions as well as catalyst and feed compositions allows one to obtain product compositions in which the selectivity of $C_{n+1}$ alcohol produced may range from as little as about two percent or lower on up to about ninety percent or higher. Selectivity is defined as being the ratio of the number of moles of carbon in a particular product produced (e.g. $C_{n+1}$ alcohol) to the total number of moles of carbon in all products, and stated as a percentage (a product being defined as any carbon-containing compound other than carbon dioxide or one of the feed gases). In general, it is preferred that the selectivity of the $C_{n+1}$ alcohol produced be at least about five percent. Accordingly, it is clear that the amount of $C_{n+1}$ alcohol produced by the process of this invention may vary widely and be effectively controlled by the appropriate conditions of the process of this invention. Likewise the rate of $C_{n+1}$ alcohol production and normal to iso (branched chain) product ratio of $C_{n+1}$ alcohol produced can also be pre-determined by control of the appropriate conditions involved. Further, the formation of various by-products may be desirably minimized by selection of appropriate catalyst composition, feed compositions and reaction conditions.

It is generally desirable to control the reaction conditions to minimize formation of by-products. The most prevalent non-alcohol by-product is the $C_n$ hydrocarbon hydrogenation product although other hydrocarbons may also be produced. Preferably hydrocarbon by-products are produced in amounts, relative to total alcohol production, of less than about twenty mole percent. Other possible by-products may include various oxygenated compounds such as aldehydes, esters and ketones. Such oxygenated by-products are preferably produced in amounts, relative to the total alcohol production of less than about ten mole percent, optimally less than about five mole percent. Formation of such by-products may be minimized by selection of appropriate catalyst conditions, feed compositions and reaction conditions. In addition, the conversion of synthesis gas directly to $C_1$-$C_5$ alcohols, as described in the above mentioned application, Ser. No. 567,243, is clearly suppressed by this invention due to the presence of the olefin in the feed to the reaction and indeed may be completely suppressed under appropriate circumstances. Moreover, the degree of such suppression of the formation of $C_1$-$C_5$ alcohols directly from synthesis gas by the practice of this invention can vary depending upon the conditions, e.g. reaction conditions and catalyst composition employed, and it is the control over such conditions that allows one, by the practice of this invention to reduce the production of alcohols other than $C_{n+1}$ alcohols to any degree desirable, e.g. from one mole percent on up to one hundred mole percent. In general it is preferred to produce an alcohol product containing from ten to one hundred mole percent of $C_{n+1}$ alcohol based on the total amount of all alcohol present in said product.

The reaction of the present invention is conducted in the vapor phase by reacting a gas feed of one or more $C_n$ olefins with carbon monoxide and hydrogen in the presence of the solid, heterogeneous molybdenum sulfide-alkali metal and/or alkaline earth metal catalyst. The desired $C_{n+1}$ alcohol may be separated and recovered from the gaseous reaction products by any suitable technique known to those skilled in the art. In addition, any conventional equipment may be employed in the process of the invention, with suitable regard for the reactants, conditions of reaction and products.

The carbon monoxide and hydrogen reactants may conveniently be derived from so-called synthesis gas which is primarily a mixture of carbon monoxide and hydrogen, although it may typically also contain a very small amount of sulfur compounds as well as small amounts of carbon dioxide, and nitrogen and other inert gases, depending on its source. Synthesis gas is produced commercially, for example, as a product of the partial combustion of coal, natural gas, petroleum bottoms or other carbonaceous materials. A specific method of synthesis gas derivation is the heating of coke in the presence of air and then steam. The molar ratio of carbon monoxide to hydrogen ($CO:H_2$) in synthesis gas may vary widely from about 1:10 to about 10:1, for purposes of the present invention, the preferred molar ratio $CO:H_2$ in the gas feed to the reaction is from about 2:1 to about 1:1. Of course, rather than employ synthesis gas, which is the preferred source of the carbon monoxide and hydrogen reactants, any other gas containing predominantly carbon monoxide and hydrogen within the foregoing ratios may be employed. Regardless of the source of the carbon monoxide and hydrogen reactants, the amount of total carbon monoxide and hydrogen in the total gas feed to the reaction is not critical, and may generally be within the range of about 10 to about 98 volume percent of the total gas feed, preferably from about 50 to about 98 volume percent. It has been observed that, in producing butanol from propylene, increases in the carbon monoxide partial pressure in the total feed gas tend to increase the selectivity of the catalyst to butanol and decrease selectivity to the hydrogenation product, propane. Therefore, it is preferred that carbon monoxide be present in the total gas feed to the reaction in an amount at least equal to the amount of hydrogen. It is expected that the total gas feed to the reaction may also contain small amounts of sulfur compounds without deactivating substantially the molybdenum sulfide-alkali catalyst.

The total gas feed to the reaction also contains one or more $C_n$ olefins and may contain an inert gas such as nitrogen. In general, the amount of olefin gas feed may be within the range of about 2 to about 95 volume percent of the total gas feed and preferably ranges from about 2 to about 30 volume percent. Of course, it is to be understood that while it may be preferred to employ a gas feed mixture of olefin, carbon monoxide and hydrogen, the use of such mixtures is not critical and each individual gas may be fed to the reaction independently from the other, if desired.

The catalyst consists essentially of molybdenum sulfide and a compound (i.e., an "alkali compound") selected from the group consisting of alkali metal and alkaline earth metal compounds and mixtures thereof. The precise catalytic specie or species are not known with certainty. It is possible that operating temperatures and pressures and catalyst preparation methods, as well as the feed gases, may have an effect on the structure or activity of the catalyst. The precise effects are not readily ascertainable and are difficult to measure. For this reason, it is not possible to describe with reasonable certainty the structure of the active catalytic specie or species. However it is known that when the molybdenum sulfide precursor of such catalysts is prepared by methods described hereinbelow, it exhibits an X-ray diffraction pattern characteristic of crystalline molybdenum disulfide. For ease of description, the molybdenum will be described herein as the sulfide. Subsequently, the alkali compound is added to that molybdenum sulfide to provide the highly selective catalyst of the invention. For purposes of the present invention, it is sufficient if the alkali compound is added as described herein, regardless of the particular form it may take in the active catalyst. The alkali compound may be added to the molybdenum sulfide by the so-called incipient wetness technique, known to those skilled in the art, and described hereinbelow. The resulting catalyst is said to consist essentially of molybdenum sulfide and an alkali compound selected from the group consisting of an alkali metal compound, an alkaline earth metal compound and mixtures thereof.

However, the form of the alkali compound in the active catalytic system may not be the same as the alkali compound that was introduced to the molybdenum sulfide. The amount of alkali compound in the molybdenum sulfide catalyst is not critical but does have an influence on the type of products obtained. In general catalysts containing from about 0.05 to about 1.0 mole of alkali compound per mole of molybdenum should be sufficient for most purposes although higher and lower amounts may be employed. Preferably the catalyst contains from about 0.2 to about 0.6 mole of alkali compound per mole of molybdenum.

The catalyst may be prepared by conventional means, such as by adding an alkali compound to a sulfur-containing molybdenum compound such as $MoS_3$, $MoS_2$, ammonium oxythiomolybdate or ammonium polythiomolybdate (which compounds may be obtained commercially or prepared from a variety of molybdenum compounds) by, for example, impregnation with a solution of the alkali compound (i.e., an incipient wetness technique); by grinding and calcining a dry alkali compound with the molybdenum compound; co-precipitation; or ion exchange. Another method of preparing the catalyst comprises sulfiding an alkali molybdate or a molybdenum oxide such as $MoO_2$ or $MoO_3$, after treatment with an alkali compound. A preferred method of preparing the catalyst comprises decomposing a thiomolybdate salt to produce molybdenum sulfide (e.g., as described in U.S. Pat. Nos. 4,253,553 and 4,243,554) and then adding the alkali compound by a suitable technique, such as the incipient wetness method.

More specifically, in a preferred method, molybdenum sulfide may be prepared by decomposing a thiomolybdate salt, such as ammonium thiomolybdate ("ATM") or ammonium polythiomolybdate, at an elevated temperature (e.g., on the order of about 300°–600° C.) in a gaseous atmosphere such as nitrogen, hydrogen, or mixtures thereof. Other gases may be employed, such as an inert gas, carbon monoxide, etc. The ammonium thiomolybdate or other salt may be prepared by known methods, such as (in the case of ammonium thiomolybdate) by bubbling hydrogen sulfide through an ammonium hydroxide solution of ammonium hepta molybdate, $(NH_4)_6Mo_7O_{24}.4H_2O$, at elevated temperatures (e.g., about 30°–40° C.). The alkali compound may be added to the molybdenum sulfide by the so-called incipient wetness technique known to those skilled in the art. This technique generally comprises adding a solution of the alkali compound to the dry molybdenum sulfide, under vacuum, followed by drying at elevated temperature under an inert gas such as nitrogen. If the amount of alkali compound that can be added to the molybdenum sulfide is less than desired because of limited solubility of the particular alkali compound employed, the procedure may be repeated until the desired alkali compound to molybdenum ratio is obtained.

The particular alkali compound contained in the catalyst of the invention does have an effect upon the alcohol selectivity of that catalyst. Generally, those compounds may be selected from inorganic and organic salts, oxides, sulfides and hydroxides of alkali metals and alkaline earth metals and mixtures thereof. It is expected that all organic and inorganic salts of alkali metals will form catalysts which can give good selectivity to alcohols. Examples of suitablef inorganic salts are the nitrates, sulfates, carbonates and chlorides of the alkali metals (e.g., sodium, potassium, lithium, cesium and rubidium) or alkaline earth metals (e.g., magnesium, calcium, barium and strontium); examples or suitable organic salts are the acetates, methoxides, ethoxides, tartrates and citrates of the alkali metals or alkaline earth metals. Specific examples of suitable alkali metal and alkaline earth metal compounds useful in this invention include potassium acetate, potassium nitrate, cesium acetate, lithium nitrate, rubidium acetate, barium hydroxide, magnesium acetate and the like. Among the various alkali and alkaline earth metals, the potassium, cesium, rubidium, lithium, magnesium and barium compounds are preferred, particularly the potassium compounds.

The solid catalyst may be employed in any convenient form depending upon the conditions of reaction and the equipment employed. For example, the catalyst, normally obtained as a powder by grinding or milling, may be made into other conventional forms such as pellets, tablets, granules, and the like by known methods, or may be supported on any suitable inert support. On a commercial scale, it probably would be desirable to use large mesh. In the case of fluidized-bed operations, a powdered catalyst of suitable size may be appropriate. Those skilled in the art will be able to practice the invention by selecting the form and size of catalyst, based on the conditions encountered in use. If a supported catalyst is desired, any typical inert support may be employed, such as carbon, silica, alumina, titania, silica-alumina, silica-titania, magnesia, molecular sieves, zeolites, clays, and the like. The supported catalysts may be prepared by techniques analogous to those employed for the unsupported catalysts, such as an incipient wetness technique using ammonium hepta molybdate and potassium acetate in aqueous solution and the molybdate-potassium precursor sulfided in situ with $H_2S$ after drying and calcination. Supported catalysts or pelletized or extruded unsupported catalysts are favored in large-scale, fixed-bed systems. Slurry systems are conveniently operated with finer catalyst particles. The use and selection of supported or unsupported catalyst systems to suit various reactor systems is readily understood by those skilled in the art.

To produce the desired $C_{n+1}$ alcohols, a gas feed of at least one $C_n$ olefin is reacted with carbon monoxide and hydrogen in the vapor phase in suitable equipment, in the presence of catalyst, under suitable conditions of gas hourly space velocity (GHSV), temperature and pressure.

The GHSV of the total feed gas is defined as the total volume of gases fed per volume of catalyst charge per hour (expressed as reciprocal hours, $hr^{-1}$). For purposes of the present invention, the GHSV may be from about 300 to about 40,000 $hr^{-1}$, preferably from about 1,000 to about 24,000 $hr^{-1}$, and more preferably from about 3,000 to about 24,000 $hr^{-1}$.

The maximum GHSV will depend in part on the economics of the equipment used. With high GHSV's, alcohol selectivity is not substantially changed but total conversion to product may tend to drop off. Therefore, there is no particular advantage to using very high GHSV's. Generally, however, to obtain good rates of $C_{n+1}$ alcohol production, it is most preferred that the GHSV be from about 6,000 to about 24,000 $hr^{-1}$.

The temperature at which the process of the invention may be performed is not particularly critical and may be varied depending on the results desired. As a general rule, the reaction temperature may be from about 200° C. to about 350° C., and a temperature of from about 240° C. to about 350° C. is preferred. When temperatures higher than those used, $C_{n+1}$ alcohol selectivity may decrease and a larger proportion of $C_n$ saturated hydrocarbons may be produced.

The pressure of the reaction is not critical and may be from about atmospheric to about 2,000 psig, depending on the equipment used and results desired. Generally, higher pressures may tend to favor better $C_{n+1}$ alcohol selectivity. The examples which follow are meant to illustrate the present invention and are intended to enable those skilled in the art to practice the present invention. They are not intended to limit the invention. Rather, it is intended that the invention be limited only by the scope of the claims appended hereto.

In the examples (all of which describe work actually performed), the unsupported catalyst was prepared by decomposing ammonium thiomolybdate (ATM) at a temperature of about 400° C. in an atmosphere of 10 volume % hydrogen in nitrogen. The ATM was prepared by bubbling hydrogen sulfide through an ammonium hydroxide solution of ammonium hepta molybdate at 30°-40° C. The molybdenum sulfide prepared in this manner exhibited an X-ray diffraction pattern typical of molybdenum disulfide and surface areas of 10-60 square meters/gram. The alkali compounds were then introduced into the molybdenum sulfide by an incipient wetness technique. Specifically, the molybdenum sulfide was first evacuated for one hour using a rotary vacuum pump and then an aqueous solution of the additive was introduced onto the molybdenum sulfide with a syringe. The volume of solution added was equivalent to the pore volume of the molybdenum sulfide (i.e., a volume required to fill the void volume of the molybdenum sulfide). If excess liquid was present, the catalyst was vacuum-dried until no liquid was present. The resulting material was then dried under a flow of nitrogen gas at 85° C. for one hour and then under a flow of nitrogen gas at a temperature of 110° C. for two hours. The material was then ground to break up the clumps of material and calcined under a flow of 10 volume percent of hydrogen in nitrogen at 400° C. for 1 hour.

Supported catalysts in the Examples were prepared by the incipient wetness technique using ammonium hepta molybdate and potassium acetate in an aqueous solution and $Al_2O_3$ as the support material. The molybdate-potassium precursor being sulfided with $H_2S$ for 1 hour at 400° C. after drying and calcination.

The reactor used in the examples was a continuous feed, stainless steel, U-shaped, tubular reactor with no recycle. For most of that work, the reactor was equipped with mass flow controllers on separate olefin, carbon monoxide, hydrogen and nitrogen feed lines. The reactor tube was ⅜ths inch in diameter. Product identification was accomplished by conventional gas chromatography and mass spectroscopy.

The procedure used in all examples was generally the same. Before initiating a run, the catalyst was loaded into the U-tube reactor with 0.5 mm quartz beads above and below the catalyst bed. If the catalyst was an unsupported catalyst in fine powder form, it was first mixed with an equal volume of quartz beads. Otherwise, supported 20-40 mesh particles were used. Once the catalyst was installed in the reactor, the reactor was pressure-tested and then flushed several times with nitrogen gas before the feed gas flows were started. After the desired gas feed flows and pressure were established, the reactor was heated to reaction temperatures in a fluidized sand bath. The effluent gas reaction products were analyzed by gas chromatography. The data shown in the examples represents an average of several analyses.

In the examples, the following definitions are used: Selectivity is the ratio of the number of moles of carbon in a particular product produced to the total number of moles of carbon in all products, stated as a percentage. A product is defined as any carbon-containing compound other than $CO_2$ or one of the feed gases. Conversion is the ratio of the number of moles of olefin-derived products (i.e., any product containing at least as many carbon atoms as the feed olefin) to the number of moles of olefin fed, stated as a percentage.

EXAMPLES 1 AND 2

These examples generally illustrate the ability of the process of the present invention to convert $C_n$ olefins to $C_{n+1}$ alcohols employing a catalyst consisting essentially of molybdenum sulfide and potassium acetate in a 1 to 1 molar ratio, made as described above. Example 1 was run as described above at a temperature of 250° C., a pressure of 400 psig, a GHSV of 12,000 $hr^{-1}$ with a gas feed of 10% by volume ethylene in a 1:1 (molar) mixture of CO and $H_2$ [$H_2$:CO:ethylene=4.5:4.5:1]. Example 2 was run at 120 psig, 250° C., a GHSV of 12,000 $hr^{-1}$ with a gas feed of 20% by volume propylene in a 1:1 (molar) mixture of CO and $H_2$ [$H_2$:CO:ethylene=2:2:1]. The results are shown in Table I below.

TABLE I

| | | Selectivity[a] | | | | | | | | |
|---|---|---|---|---|---|---|---|---|---|---|
| Example | Olefin | MeOH | EtOH | PrOH | iBuOH | nBuOH | others | $C_2H_6$ | $C_3H_8$ | H.C. |
| 1 | $C_2H_4$ | 7.3 | 2.2 | 62 | | | 9 | 8.4 | 1.7 | 5.4 |

TABLE I-continued

| Example | Olefin | MeOH | EtOH | PrOH | iBuOH | nBuOH | others | $C_2H_6$ | $C_3H_8$ | H.C. |
|---------|--------|------|------|------|-------|-------|--------|----------|----------|------|
| 2 | $C_3H_4$ | | | | 5.6 | 26 | 12 | | (b) | 53 |

Selectivity[a]

[a]MeOH = methyl alcohol, EtOH = ethyl alcohol, PrOH = propyl alcohol, iBuOH = iso-butyl alcohol, nBuOH = n-butyl alcohol, others = other oxygenated products such as aldehydes, esters and ketones, $C_2H_6$ = ethane, $C_3H_8$ = propane, H.C. = hydrocarbons other than $C_2$'s and $C_3$'s.
[b]Propane could not be analyzed for because of overlap with the propylene in the feed.

EXAMPLES 3–49

Propylene was reacted with synthesis gas under various reaction conditions using catalysts consisting essentially of molybdenum sulfide and 0.6 mole of various alkali compounds per mole of molybdenum. The reaction conditions, alkali compounds and results are set forth in Table II. The symbols mean the same as in Table I. Unless otherwise noted, the gas feed molar ratio $H_2:CO:C_3H_6$ was 4.5:4.5:1.

propylene was reacted with synthesis gas using catalysts consisting essentially of molybdenum sulfide and various amounts of potassium acetate per mole of molybdenum. The reaction conditions were: a temperature of 290° C., a pressure of 170 psig, a GHSV of 12,000 $hr^{-1}$ and a $CO:H_2:C_3H_6$ gas feed of 2:2:1 (molar). The results are set forth in Table III and the symbols mean the same as in Tables I and II.

As can be seen from this data, higher amounts of potassium acetate decreased percent conversion while

TABLE II

| Example | Alkali Compound | Temp (°C.) | Pressure (psig) | GHSV ($hr^{-1}$) | Selectivities (%) BuAld[b]+ BuOH | BuOH | Conversion (%) | Rate of BuOH[c] Production |
|---------|-----------------|------------|-----------------|------------------|--------------|------|----------------|---------------------------|
| 3 | $LiNO_3$ | 280 | 410 | 8000 | 16.0 | 16.0 | 1.5 | 2.30 |
| 4 | $LiNO_3$ | 320 | 700 | 8000 | 12.6 | 11.7 | 3.2 | 4.92 |
| 5 | $LiNO_3$ | 260 | 700 | 8000 | 54.2 | 54.0 | 2.6 | 3.99 |
| 6 | $LiNO_3$ | 320 | 110 | 8000 | 0.3 | 0.3 | 0.04 | 0.06 |
| [a]7 | $LiNO_3$ | 320 | 180 | 4000 | 2.4 | 2.3 | 0.1 | 0.08 |
| 8 | Rb acetate | 280 | 410 | 8000 | 31.1 | 31.1 | 2.7 | 4.15 |
| 9 | Rb acetate | 320 | 700 | 8000 | 6.2 | 5.7 | 2.7 | 4.15 |
| 10 | Rb acetate | 250 | 700 | 8000 | 35.5 | 35.5 | 2.1 | 3.26 |
| 11 | Rb acetate | 320 | 110 | 8000 | 3.5 | 3.0 | 0.2 | 0.31 |
| [a]12 | Rb acetate | 320 | 165 | 4000 | 9.5 | 9.0 | 0.2 | 0.31 |
| 13 | Mg acetate | 285 | 410 | 8000 | 9.5 | 9.4 | 4.9 | 7.53 |
| 14 | Mg acetate | 320 | 680 | 8000 | 3.2 | 2.9 | 3.8 | 5.84 |
| 15 | Mg acetate | 250 | 660 | 8000 | 20.1 | 20.1 | 1.1 | 1.69 |
| 16 | Mg acetate | 320 | 110 | 8000 | 2.0 | 2.0 | 1.2 | 1.84 |
| 17 | Mg acetate | 250 | 100 | 8000 | 8.3 | 8.3 | 0.2 | 0.31 |
| 18 | $KNO_3$ | 289 | 410 | 8000 | 48.5 | 45.1 | 2.1 | 3.23 |
| 19 | $KNO_3$ | 320 | 610 | 8000 | 14.5 | 13.4 | 3.7 | 5.68 |
| 20 | $KNO_3$ | 250 | 600 | 8000 | 58.0 | 57.4 | 2.3 | 3.53 |
| [a]21 | $KNO_3$ | 320 | 140 | 4000 | 5.6 | 4.1 | 0.1 | 0.08 |
| 22 | $KNO_3$ | 285 | 460 | 8000 | 9.0 | 9.0 | 2.9 | 4.45 |
| 23 | $KNO_3$ | 320 | 700 | 12000 | 4.3 | 3.2 | 2.4 | 5.54 |
| 24 | $KNO_3$ | 250 | 700 | 12000 | 49.9 | 49.5 | 4.5 | 10.37 |
| 25 | $KNO_3$ | 320 | 700 | 4000 | 4.1 | 3.0 | 2.7 | 2.08 |
| 26 | $KNO_3$ | 285 | 460 | 8000 | 31.3 | 29.9 | 4.9 | 7.53 |
| 27 | $KNO_3$ | 320 | 120 | 12000 | 7.2 | 7.2 | 0.8 | 1.85 |
| 28 | $KNO_3$ | 320 | 120 | 4000 | 9.5 | 9.1 | 1.6 | 1.23 |
| 29 | $KNO_3$ | 285 | 460 | 8000 | 19.7 | 18.2 | 3.8 | 5.84 |
| 30 | $KNO_3$ | 250 | 120 | 12000 | 22.6 | 22.6 | 0.3 | 0.69 |
| 31 | $KNO_3$ | 250 | 120 | 4000 | 26.1 | 26.1 | 0.8 | 0.61 |
| 32 | $KNO_3$ | 280 | 470 | 8000 | 12.4 | 12.2 | 3.8 | 5.84 |
| 33 | $KNO_3$ | 320 | 700 | 12000 | 5.4 | 4.6 | 4.4 | 6.76 |
| 34 | $KNO_3$ | 250 | 700 | 12000 | 41.4 | 37.3 | 4.3 | 6.60 |
| 35 | K acetate | 250 | 110 | 8000 | 31.3 | 31.3 | 0.6 | 0.92 |
| 36 | K acetate | 250 | 500 | 8000 | 54.8 | 49.3 | 3.7 | 5.68 |
| 37 | K acetate | 260 | 110 | 8000 | 82.4 | 82.4 | 3.3 | 5.07 |
| 38 | K acetate | 260 | 700 | 8000 | 21.8 | 21.6 | 2.1 | 3.23 |
| 39 | K acetate | 280 | 410 | 8000 | 32.1 | 31.9 | 4.5 | 6.91 |
| 40 | K acetate | 320 | 110 | 8000 | 28.0 | 26.9 | 3.8 | 5.84 |
| 41 | K acetate | 320 | 110 | 8000 | 38.1 | 37.0 | 6.4 | 9.83 |
| 42 | K acetate | 320 | 550 | 8000 | 2.9 | 2.3 | 2.2 | 3.38 |
| 43 | K acetate | 320 | 700 | 8000 | 5.6 | 3.4 | 1.9 | 2.92 |
| [a]44 | K acetate | 320 | 200 | 4000 | 31.0 | 28.2 | 1.8 | 1.38 |
| 45 | Cs acetate | 280 | 410 | 8000 | 26.0 | 25.9 | 3.2 | 4.92 |
| 46 | Cs acetate | 320 | 700 | 8000 | 6.2 | 6.0 | 2.1 | 3.23 |
| 47 | Cs acetate | 260 | 700 | 8000 | 51.6 | 51.6 | 2.2 | 3.38 |
| 48 | Cs acetate | 320 | 110 | 8000 | 16.2 | 16.1 | 0.6 | 0.92 |
| [a]49 | Cs acetate | 320 | 200 | 4000 | 31.2 | 28.4 | 1.4 | 2.15 |

[a]The molar ratio $CO:H_2:C_3H_6$ in the feed was 3.5:3.5:3
[b]BuAld = butyraldehyde
[c]Rate = total pounds of BuOH (i.e., all butanols) produced per cubic foot of catalyst charge per hour

EXAMPLES 50–53

These examples illustrate the effect on selectivity of the alkali concentration. In each of these examples, selectivity to butanol was increased. Conversely, lower amounts of potassium acetate increased percent conversion while selectivity to butanol was decreased and the amount of hydrogenation products (i.e., the $C_n$ saturated hydrocarbons) increased.

invention employing propylene. The gas feed $H_2:CO:C_3H_6$ molar ratio was 4.5:4.5:1. The catalyst consisted essentially of molybdenum sulfide and 0.6 mole of potassium nitrate per mole of molybdenum. The GHSV was 12,000 hr$^{-1}$. The results are set forth in Table VI and the symbols mean the same as in Tables I and II.

TABLE III

| Example | Moles K per mole molybdeum | % Conv. | Selectivity (%) | | | | | |
|---|---|---|---|---|---|---|---|---|
| | | | nBuOH | iBuOH | BuAld | $C_3H_8$ | H.C. | MeOH + EtOH |
| 50 | 0.05 | 4.85 | 1.6 | 0.6 | ND | 88.0 | 9.8 | ND |
| 51 | 0.10 | 2.3 | 7.4 | ND | 0.3 | 75.4 | 11.1 | 4.7 |
| 52 | 0.40 | 0.28 | 5.8 | 1.5 | 0.3 | 29.2 | ND | 53.1 |
| 53 | 0.60 | 0.23 | 27.4 | 2.1 | ND | 46.5 | 3.7 | 19.3 |

ND = not detected.

EXAMPLES 54–56

Propylene was reacted with synthesis gas over a catalyst consisting essentially of molybdenum sulfide and 0.2 mole of potassium hydroxide, per mole of molybdenum. The reaction conditions were: temperature = 290° C.; pressure = 170 psig; and GHSV = 12000 hr$^{-1}$. The various gas feed ratios $H_2:CO:C_3H_6:N_2$ and the reaction conditions and results are shown in Table IV. The symbols mean the same as in Tables I and II.

TABLE IV

| Example | $H_2:CO:C_3H_6:N_2$ (molar) | Conv. % | Selectivity (%) | | | | | |
|---|---|---|---|---|---|---|---|---|
| | | | nBuOH | iBuOH | BuAld | $C_3H_8$ | H.C. | MeOH + RtOH |
| 54 | 42:39:17:1 | 1.9 | 19.2 | 4.4 | 1.0 | 48.2 | 12.3 | 14.0 |
| 55 | 16:34:19:30 | 0.8 | 15.5 | 3.7 | 2.2 | 59.5 | 14.0 | 4.0 |
| 56 | 32:50:16:1 | 1.4 | 22.3 | 3.0 | 1.6 | 44.7 | 11.6 | 14.7 |

EXAMPLES 57–59

These examples, which illustrate the effect of temperature on the process of the present invention, were run employing a supported catalyst prepared by the incipient wetness technique using ammonium hepta molybdate (24 wt. % Mo) and potassium acetate (1.9 wt. % K) in an aqueous solution and $Al_2O_3$ [Norton ® SA5534] as the support material. After drying and calcination the molybdate-potassium precursor was sulfided in situ with $H_2S$ for 1 hour at 400° C. before use. The remaining reaction conditions were: a pressure of 170 psig, a GHSV of 12,000 hr$^{-1}$ and a $H_2:CO:C_3H_6$ gas feed of 3:5:3.5:1 (molar). The results are set forth in Table V and the symbols mean the same as in Tables I and II.

As can be seen from this data, higher operating temperatures tend to decrease selectivity toward $C_{n+1}$ alcohols and increase selectivity toward hydrocarbons, including $C_n$ saturated hydrocarbons.

TABLE V

| Example | Temp. (°C.) | Conv. % | Selectivity (%) | | | | | |
|---|---|---|---|---|---|---|---|---|
| | | | nBuOH | iBuOH | BuAld | $C_3H_8$ | H.C. | MeOH + EtOH |
| 57 | 250 | 0.45 | 22.4 | 4.8 | ND | 60.7 | 6.7 | 1.7 |
| 58 | 290 | 0.81 | 24.1 | 5.0 | 1.0 | 51.6 | 10.8 | 5.6 |
| 59 | 320 | 1.05 | 15.3 | 3.6 | 1.2 | 58.9 | 15.2 | 5.0 |

ND = not detected

EXAMPLES 60–63

These examples illustrate the effect of pressure, at different temperatures, on the process of the present

TABLE VI

| Example | Pressure (psig) | Temperature (°C.) | Conversion (%) | BuOH Selectivity (%) | Rate of BuOH Production |
|---|---|---|---|---|---|
| 60 | 120 | 250 | 0.3 | 22.6 | 0.69 |
| 61 | 700 | 250 | 4.3 | 37.3 | 6.60 |
| 62 | 120 | 320 | 0.8 | 7.2 | 1.85 |
| 63 | 700 | 320 | 2.4 | 3.2 | 5.54 |

EXAMPLES 64–65

These examples illustrate the selective production of propanol from ethylene by the process of the present invention employing a total gas feed of ethylene, hydrogen and carbon monoxide, as compared to the lack of such production when the process is carried out in the absence of ethylene starting material in the total gas feed. The processes were carried out in the presence of a catalyst consisting essentially of molybdenum sulfide and 1.0 mole of potassium nitrate per mole of molybdenum; 400 psig and a GHSV of 12,000 hr$^{-1}$. The total gas feed $H_2:CO$ molar ratio of Example 64 was 1:1, while the total gas feed $H_2:CO:C_2H_4$ molar ratio of Example 65 was 4.5:4.5:1. The results are set forth in Table VII and the symbols mean the same as defined in Table I.

TABLE VII

| Example | Ethylene (%) | Temp. (°C.) | Selectivity (%) | | | | | | |
|---|---|---|---|---|---|---|---|---|---|
| | | | MeOH | EtOH | PrOH | others | $C_2H_6$ | $C_3H_8$ | H.C. |
| 64 | 0 | 300 | 47.3 | 26.5 | 6.9 | 0 | 2.0 | 0.9 | 16.4 |
| 65 | 10 | 250 | 7.2 | 2.3 | 62.0 | 8.6 | 8.4 | 2.0 | 9.5 |

EXAMPLES 66-67

These examples illustrate the selective production of propanol from ethylene by the process of the present invention employing a total gas feed of ethylene, hydrogen and carbon monoxide, as compared to the lack of such production when the process is carried out in the absence of ethylene starting material in the total gas feed. The processes were carried out in the presence of a catalyst consisting essentially of molybdenum sulfide and 0.36 mole of sodium nitrate per mole of molybdenum; 400 psig and GHSV of 12,000 hr$^{-1}$. The total gas feed $H_2$:CO molar ratio of Example 66 was 1:1, while the total gas feed $H_2$:CO:$C_2H_4$ molar ratio of Example 67 was 4.5:4.5:1. The results are set forth in Table VIII and the symbols mean the same as defined in Table I.

TABLE VIII

| Example | Ethylene (%) | Temp. (°C.) | Selectivity (%) | | | | | | |
|---|---|---|---|---|---|---|---|---|---|
| | | | MeOH | EtOH | PrOH | others | $C_2H_6$ | $C_3H_8$ | H.C. |
| 66 | 0 | 270 | 51.2 | 22.5 | 5.9 | 0 | 3.9 | 2.4 | 14.1 |
| 67 | 10 | 250 | 3.2 | 1.6 | 51.8 | 19.8 | 16.4 | 1.6 | 5.6 |

EXAMPLES 68-69

These examples illustrate the selective production of propanol from ethylene by the process of the present invention when small and high amounts of ethylene are employed in the gas feed. The processes were carried out in the presence of a supported catalyst prepared by the incipient wetness technique using ammonium hepta molybdate (24 wt. % Mo) and potassium acetate (3.7 wt. % K) in an aqueous solution and $Al_2O_3$ [Norton ® SA6173] as the support material. After drying and calcination the molybdate-potassium precursor was sulfided in situ with $H_2S$ for 1 hour at 400° C. before use. Example 68 employed an ethylene:CO:$H_2$ gas feed molar ratio of 1:4.5:4.5 and Example 69 employed an ethylene:CO:$H_2$ gas feed molar ratio of 9:0.5:0.5. Both examples employed a temperature of 250° C., a pressure of 400 psig. and a GHSV of 12,000 hr$^{-1}$ as the reaction conditions. The results are set forth in Table IX.

The data shows that a low ethylene content in the total gas feed increases propanol production and decreases $C_n$ hydrocarbon and ketone by-product, while a high ethylene content in the total gas feed decreases propanol production and increases $C_n$ hydrocarbon and ketone by-product.

olefin with carbon monoxide and hydrogen in the presence of a solid catalyst consisting essentially of molybdenum sulfide and an alkali compound selected from the group consisting of alkali metal and alkaline earth metal compounds and mixtures thereof, and wherein the reaction gas hourly space velocity is from about 1,000 to about 24,000 hour$^{-1}$.

2. The process of claim 1 wherein said $C_n$ olefin is a terminal olefin.

3. The process of claim 2 wherein said olefin has at least 2 carbon atoms.

4. The process of claim 2 wherein said olefin is propylene and said $C_{n+1}$ alcohol is butanol.

5. The process of claim 4 wherein the normal to iso ratio of butanol product is at least about 5.

6. The process of claim 1 wherein said alkali compound is selected from the group consisting of inorganic and organic salts, oxides, sulfides and hydroxides of alkali metals and alkaline earth metals and mixtures thereof.

7. The process of claim 6 wherein said alkali compound is selected from the group consisting of the hydroxides, nitrates and acetates of potassium, cesium, rubidium, lithium, magnesium and barium, and mixtures thereof.

8. The process of claim 4 wherein said alkali compound is a nitrate, hydroxide or acetate of potassium.

9. The process of claim 3 wherein said alkali compound is a nitrate, hydroxide or acetate of potassium.

10. The process of claim 3 wherein said alkali compound is selected from the group consisting of potassium compounds and cesium compounds.

11. The process of claim 1 wherein said alkali compound is present in said catalyst in an amount of at least about 0.2 mole per mole of molybdenum.

12. The process of claim 1 wherein said alkali compound is present in said catalyst in an amount of from about 0.2 to about 0.6 mole per mole of molybdenum.

13. The process of claim 1 wherein the temperature of reaction is from about 200° to about 350° C.

14. The process of claim 1 wherein the reaction is

TABLE IX

| No. | Ethylene (%) | Selectivity (%) | | | | | | | | | | | |
|---|---|---|---|---|---|---|---|---|---|---|---|---|---|
| | | MeOH | EtOH | PrOH | BuOH | $CH_4$ | $C_2H_6$ | $C_3H_6$ | $C_3H_8$ | H.C. | DEK | PP | Other |
| 68 | 10 | 0.1 | 0.1 | 7.7 | 0.4 | 0.3 | 71.3 | 3.5 | 1.2 | 1.9 | 1.0 | 12.0 | 0.5 |
| 69 | 90 | 0.001 | 0.01 | 4.8 | 01 | 0.06 | 83.7 | 0.2 | 0.04 | 1.1 | 7.9 | 1.0 | 1.4 |

MeOH = methyl alcohol, EtOH = ethyl alcohol, PrOH = propyl alcohol, BuOH = n butyl alcohol, $CH_4$ = methane, $C_2H_6$ = ethane, $C_3H_6$ = propylene, $C_3H_8$ = propane, H.C. = other hydrocarbons, DEK = diethylketone, PP = propylpropionate, Other = other oxygenated products.

What is claimed is:

1. A process for producing selectively $C_{n+1}$ alcohols, wherein n is a positive integer of at least 2, comprising reacting in the vapor phase a gas feed of at least one $C_n$ conducted at a pressure of from about atmospheric to about 2,000 psig.

15. The process of claim 1 wherein the reaction gas hourly space velocity is from about 3,000 to about 24,000 hour$^{-1}$.

16. The process of claim 1 wherein the reaction gas hourly space velocity is from about 6,000 to about 24,000 hour$^{-1}$.

17. The process of claim 1 wherein the amount of said $C_n$ olefin in the total gas feed to the reaction is from about 2 to about 30 mole percent, based on the total moles of gases fed to the reaction.

18. The process of claim 1 wherein the mole ratio carbon monoxide:hydrogen in the gas fed to the reaction is from about 2:1 to about 1:1.

* * * * *